(12) United States Patent
Robertson (10) Patent No.: US 8,172,762 B2
(45) Date of Patent: May 8, 2012

(54) SIMULTANEOUS BLOOD FLOW AND HEMATOCRIT SENSOR

(75) Inventor: Timothy L. Robertson, Belmont, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 1209 days.

(21) Appl. No.: 11/897,942

(22) Filed: Aug. 31, 2007

(65) Prior Publication Data

US 2008/0058630 A1   Mar. 6, 2008

Related U.S. Application Data

(60) Provisional application No. 60/824,309, filed on Sep. 1, 2006.

(51) Int. Cl.
*A61B 5/02* (2006.01)

(52) U.S. Cl. ................. 600/506; 600/505; 600/504

(58) Field of Classification Search ........... 600/504–506
See application file for complete search history.

(56) References Cited

U.S. PATENT DOCUMENTS

| | | | |
|---|---|---|---|
| 3,949,388 A | 4/1976 | Fuller | |
| 3,996,925 A * | 12/1976 | Djordjevich | 600/506 |
| 4,635,296 A | 1/1987 | Dinsmore | |
| 4,844,076 A | 7/1989 | Lesho et al. | |
| 5,099,227 A | 3/1992 | Geiszler et al. | |
| 5,331,966 A | 7/1994 | Bennett et al. | |
| 5,513,637 A | 5/1996 | Twiss et al. | |
| 5,630,835 A | 5/1997 | Brownlee | |
| 5,697,958 A | 12/1997 | Paul et al. | |
| 5,796,827 A | 8/1998 | Coppersmith et al. | |
| 5,829,444 A | 11/1998 | Ferre et al. | |
| 5,842,977 A | 12/1998 | Lesho et al. | |
| 5,905,261 A | 5/1999 | Schotland et al. | |
| 5,914,701 A * | 6/1999 | Gersheneld et al. | 345/156 |
| 6,009,350 A | 12/1999 | Renken | |
| 6,115,636 A | 9/2000 | Ryan | |
| 6,201,387 B1 | 3/2001 | Govari | |
| 6,208,894 B1 | 3/2001 | Schulman et al. | |
| 6,211,799 B1 * | 4/2001 | Post et al. | 341/33 |
| 6,336,031 B1 * | 1/2002 | Schyndel | 455/41.2 |
| 6,359,597 B2 | 3/2002 | Haj-Yousef | |
| 6,458,086 B1 * | 10/2002 | Franco et al. | 600/526 |
| 6,505,072 B1 | 1/2003 | Linder et al. | |
| 6,574,510 B2 | 6/2003 | Von Arx et al. | |
| 6,630,833 B2 | 10/2003 | Scott | |
| 6,706,040 B2 | 3/2004 | Mahon et al. | |
| 6,754,472 B1 | 6/2004 | Williams et al. | |
| 6,766,201 B2 | 7/2004 | Von Arx et al. | |
| 6,809,701 B2 | 10/2004 | Amundson et al. | |
| 7,236,821 B2 * | 6/2007 | Cates et al. | 607/2 |

(Continued)

*Primary Examiner* — Miranda Le
*Assistant Examiner* — Meredith Weare
(74) *Attorney, Agent, or Firm* — Bozicevic, Field & Francis LLP; Bret E. Field (57) ABSTRACT

Embodiments of the present invention provide blood flow sensors that can be used for measurement of various physiological parameters under a wide array of conditions. In some embodiments, the blood flow sensor can be implanted into a blood vessel and left in place indefinitely and will unobtrusively measure and record data as the patient engages in regular daily activities. The data can later be read out by a clinician using a suitable interface. In other embodiments, the data is collected and analyzed within a data collection device implanted in or attached to the patient's body, and the collection device can report to the patient on an ongoing basis or in the form of alerts issued when conditions requiring medical intervention are detected.

17 Claims, 8 Drawing Sheets

U.S. PATENT DOCUMENTS

| | | |
|---|---|---|
| 7,245,954 B2 * | 7/2007 | Glukhovsky .................. 600/350 |
| 7,664,476 B2 * | 2/2010 | Yanagida .................... 455/188.1 |
| 2003/0036674 A1 | 2/2003 | Bouton |
| 2003/0167000 A1 | 9/2003 | Mullick et al. |
| 2003/0169132 A1 | 9/2003 | Vaiser et al. |
| 2004/0004554 A1 | 1/2004 | Srinivasan et al. |
| 2004/0024309 A1 | 2/2004 | Ferre et al. |
| 2004/0030260 A1 | 2/2004 | Arx |
| 2004/0102219 A1 | 5/2004 | Bunton et al. |
| 2004/0123871 A1 | 7/2004 | Wright et al. |
| 2004/0187875 A1 | 9/2004 | He et al. |
| 2005/0075559 A1 | 4/2005 | Houzego et al. |
| 2005/0096562 A1 | 5/2005 | Delalic et al. |
| 2005/0110700 A1 | 5/2005 | Terry |
| 2005/0134520 A1 | 6/2005 | Rawat et al. |
| 2006/0025661 A1 * | 2/2006 | Sweeney et al. .............. 600/345 |
| 2006/0178109 A1 * | 8/2006 | Takiguchi .................... 455/41.1 |
| 2008/0306359 A1 * | 12/2008 | Zdeblick et al. ............. 600/302 |

* cited by examiner

SIMULTANEOUS BLOOD FLOW AND HEMATOCRIT SENSOR

CROSS-REFERENCES TO RELATED APPLICATIONS

Pursuant to 35 U.S.C. §119 (e), this application claims priority to U.S. Provisional Application Ser. No. 60/824,309 filed Sep. 1, 2006; the disclosure of which priority application is herein incorporated by reference.

BACKGROUND OF THE INVENTION

The present invention relates in general to medical devices and techniques, and in particular to measurement of physiological parameters using dependence of blood resistivity on flow.

It has long been known that the resistivity of blood varies directly with the flow velocity and inversely with hematocrit, i.e., the percentage, by volume, of whole blood that is made up of red blood cells. (See, e.g., Hoetnik et al., *IEEE Trans. Biomed. Engr.* 51:7, 1251 (2004); Sigman et al., *Amer. J. Physiol.*, 118, 708 (1937)). The variation can be on the order of 15%, large enough to be measurable. It is generally believed that the resistivity varies due to the difference in conductivity between red blood cells (RBCs) and plasma. As blood flows, the RBCs order and deform, which disrupts currents flowing through the blood, resulting in variation in the bulk resistance of blood.

Blood flow velocity can provide an indication of a patient's physiological functioning. For instance, blood flow velocity near the heart can indicate whether the heart is operating effectively. Vessel blockages created by blood clots, plaque deposits, or the like also affect blood flow velocity, as do internal bleeding and other conditions.

Existing blood flow measurement systems exploit this property, but they are often limited to use in a clinical setting. For instance, measurements can be made by inserting appropriate sensors during catheterization and other invasive procedures, but the sensors are not designed to be left in place after such procedures are completed; consequently, data cannot be collected while the patient engages in normal daily activity outside the clinical setting. Thus, the ability to use information about blood flow to monitor or diagnose disease conditions is limited.

It would therefore be desirable to provide improved blood flow sensors capable of being used for ongoing monitoring of a patient's condition.

BRIEF SUMMARY OF THE INVENTION

Embodiments of the present invention provide blood flow sensors that can be used for measurement of various physiological parameters under a wide array of conditions. In some embodiments, the blood flow sensor can be implanted into a blood vessel and left in place indefinitely and will unobtrusively measure and record data as the patient engages in regular daily activities. The data can later be read out by a clinician using a suitable interface. In other embodiments, the data is collected and analyzed within a data collection device implanted in or attached to the patient's body, and the collection device can report to the patient on an ongoing basis or in the form of alerts issued when conditions requiring medical intervention are detected.

In one embodiment, a blood flow sensor includes a sensor module configured to apply a current between two terminals that contact the blood stream. Sensing electrodes and a differential amplifier are arranged near the terminals to detect a potential difference created by the resistivity of the blood. This potential difference is related to the resistivity, which in turn correlates with the blood flow velocity.

In another embodiment, the blood flow sensor includes a wireless transmitter configured to communicate the measured potential difference to a data collection device that may be implanted in or attached to the patient's body. The wireless transmitter advantageously uses quasi-electrostatic near-field coupling to send the data to the data collection device. At the data collection device, the data can be recorded for later reporting to a clinician, used to compute additional physiological parameters, and/or used to determine whether to take some automated action, such as alerting the patient, dispensing a dose of a medication, stimulating the heart muscle, or the like.

The blood flow measurements can be used to detect, evaluate and treat numerous conditions, examples of which are described below.

The following detailed description together with the accompanying drawings will provide a better understanding of the nature and advantages of the present invention.

DETAILED DESCRIPTION OF THE INVENTION

Embodiments of the present invention provide blood flow sensors that can be used for measurement of various physiological parameters under a wide array of conditions. In some embodiments, the blood flow sensor can be implanted into a blood vessel and left in place indefinitely and will unobtrusively measure and record data as the patient engages in regular daily activities. The data can later be read out by a clinician using a suitable interface. In other embodiments, the data is collected and analyzed within a data collection device implanted in or attached to the patient's body, and the collection device can report to the patient on an ongoing basis or in the form of alerts issued when conditions requiring medical intervention are detected.

An Implantable Blood Flow Sensor and Transmitter

One aspect of the present invention relates to blood flow sensors that can measure flow velocity and/or hematocrit (the percentage, by volume, of the patient's blood that is made up of red blood cells). These measurements can be used to detect various physiological conditions, as described below.

In some embodiments, a blood flow sensor exploits the well-known property that the resistivity of blood varies directly with the flow velocity and inversely with hematocrit, i.e., the percentage, by volume, of whole blood that is made up of red blood cells as described above. In some embodiments, the sensor is implemented at micron size scales, allowing hematocrit and flow effects to be distinguished.

Figure 1:
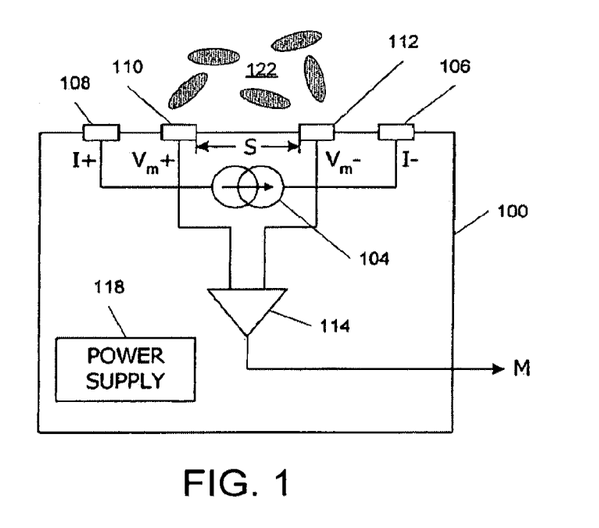
FIG. 1 is a block diagram of blood flow sensor 100 according to an embodiment of the present invention.

FIG. 1 is a block diagram of blood flow sensor 100 according to an embodiment of the present invention. Sensor 100 includes a current source 104 connected between terminals 106 and 108, sensing electrodes 110 and 112, a differential amplifier 114, and a power supply 118. Sensor 100 can be implemented, e.g., as an integrated circuit on a semiconductor substrate using conventional fabrication techniques.

Power supply 118 provides power to the components of sensor 100 (the connections are not shown but will be well understood by those of ordinary skill in the art) and may be implemented in various ways. For instance, in some embodiments, power supply 118 includes a conventional battery. In other embodiments, power supply 118 includes electrodes of two different metals exposed to the flowing blood, and power is generated through reverse electrolysis. In still other embodiments, power supply 118 collects energy from a remote source, e.g., via near-field quasi-electrostatic coupling, as described in above-referenced Application No. 60/713,680. In embodiments with a remote power source, blood flow sensor 100 can be activated at desired times by transmitting power from the remote power source. It will be appreciated that a particular power source or power supply configuration is not critical to the present invention, and a detailed description is omitted.

In operation, sensor 100 is placed inside a blood vessel, preferably at a fixed location, with terminals 106, 108 and sensing electrodes 110, 112 exposed to the flowing blood, represented in FIG. 1 by red blood cells 122. Current source 104, powered by power supply 118, applies a constant current I between terminals 106 and 108. The current passes through the blood, which has a resistivity $\rho$ that depends in part on the flow rate and in part on hematocrit. The flowing current creates a potential difference ($\Delta V$) across sensing electrodes 110, 112 that depends on the current I, the resistivity $\rho$ of the blood, and the distance S between sensing electrodes 110 and 112. In one embodiment, $\Delta V = \rho I / 2\pi S$, as described in Barber & Brown, *J. Phys. E. Sci. Instrum.*, 17, 723 (1984).

The potential difference $\Delta V$ is detected and amplified by differential amplifier 114. A measurement value M, proportional to $\Delta V$, is generated on a signal line 124.

It should be noted that the distance S between sensing electrodes 110 and 112 may be varied as desired. Where S is comparable to the size of a red blood cell (e.g., 6-8 microns), it becomes possible to count individual red blood cells flowing past. In a "cell-sized" configuration, a discrete pulse in $\Delta V$ occurs as red blood cells pass close to the device, analogous to shot noise in electronic circuits in other contexts. Amplifier 114 can be connected to a counter that counts the pulses, thereby counting red blood cells and providing a measurement of hematocrit. In some embodiments, flow velocity and hematocrit can be measured separately.

Figure 2:
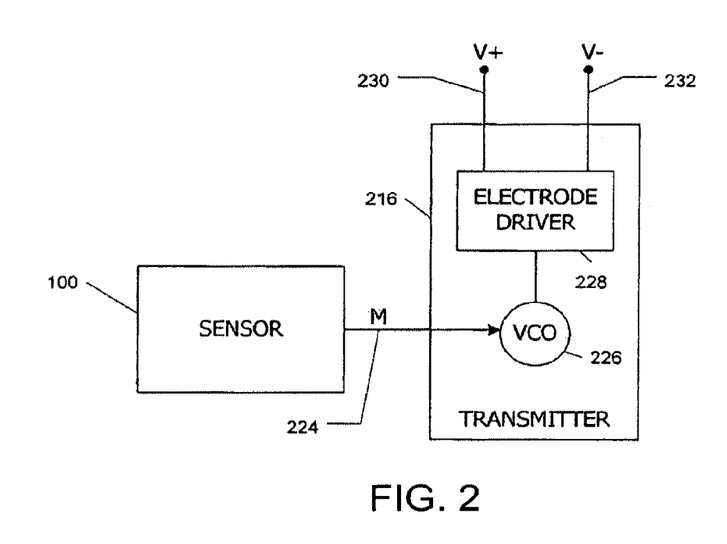
FIG. 2 is a block diagram of a transmitter for the sensor of FIG. 1 according to an embodiment of the present invention.

The measurement value M can be reported to another device located within the patient's body. In some embodiments, as shown in FIG. 2, sensor 100 is coupled to a transmitter section 216 that transmits the value M wirelessly, using quasi-electrostatic transmission techniques as described in above-referenced Application No. 60/713,680.

In one such embodiment, transmitter section 216 receives the signal M from differential amplifier 114 via line 224 and transmits the data using near-field coupling as described above. In one embodiment, transmitter section 216 transmits at a frequency determined by M. In this embodiment, transmitter section 216 includes a voltage-controlled oscillator (VCO) 226 and an electrode driver 228, which may be generally similar to the oscillator and electrode drivers described above. VCO 226 oscillates at a frequency determined by the measurement signal M, generating signals $\phi$ and $\bar{\phi}$. These signals induce electrode driver 228 to drive transmission electrodes 230, 232 at a corresponding frequency.

Transmitter section 216 may also implement other techniques for encoding and transmitting data. For instance, amplitude modulation based on the measurement data M might be substituted for frequency modulation. In another embodiment, transmitter section 216 might include an analog-to-digital converter that converts the measured signal M to a corresponding digital value. This digital value can be encoded and sent as a bit stream using amplitude modulation, frequency modulation, phase modulation, or any combination thereof. In addition, in some embodiments, an identifier of the sensor may be encoded and transmitted along with the measurement value. Transmitting an identifier allows multiple sensors placed at different locations in the patient's body to report measurements, with each reported measurement being associated with its source.

Figure 3:
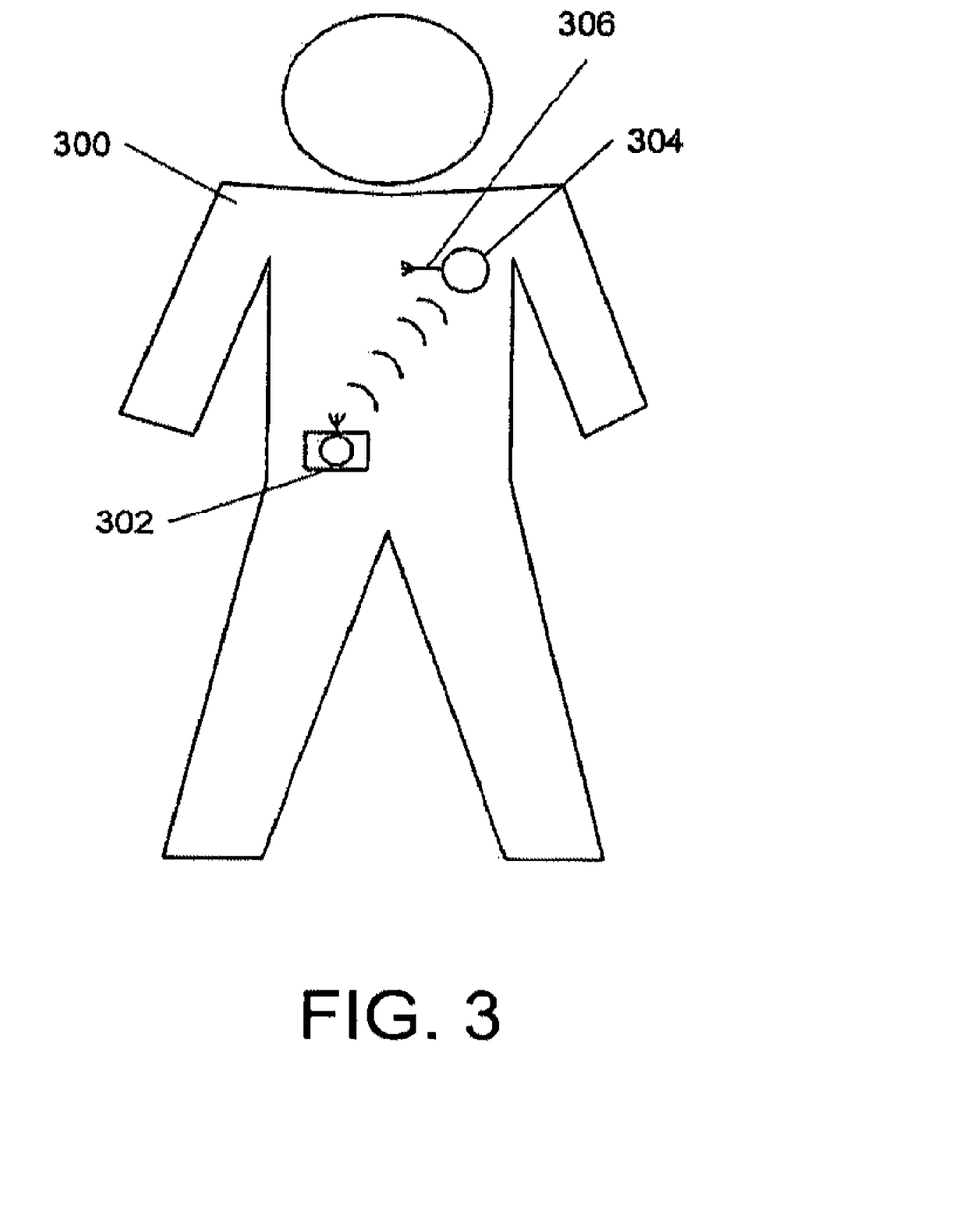
FIG. 3 illustrates an application of a blood flow sensor and transmitter according to an embodiment of the present invention.

FIG. 3 illustrates an application of a blood flow sensor and transmitter according to an embodiment of the present invention. In FIG. 3, a remote unit 302 that includes sensor 100 and transmitter section 216 (which may be fabricated together as a single integrated circuit chip using conventional techniques) is implanted in a blood vessel somewhere in the body of a patient 300. Patient 300 also has a data collection device, in this case an implanted pacemaker 304 whose leads 306 act as a receiver for signals transmitted by remote unit 302. Pacemaker 304 has a control can that stores the received data, which can then be read out by a clinician using a conventional communication wand. In other embodiments, the control can also includes logic circuits configured to process the received data and determine an action to be taken based on the data (e.g., stimulating the heart, releasing an anticoagulant into the bloodstream) and control circuits configured to perform the action determined by the logic circuits.

In another embodiment of the present invention, the inventive blood flow sensor consists of a silicon chip with 5 or more electrodes located on its surface. Two of the electrodes, which may be the outermost electrodes, are used as a current source to drive current through the fluid. The other electrodes are used as voltage sensing electrodes. The voltage difference can be measured across neighboring electrodes. Alternatively, the voltage difference can be measured across any two electrodes. The electrodes can be spaced equally apart along the sensor, to give uniformly spaced data points, and allow for easier processing of the data. Alternatively, the electrodes can be spaced at different intervals to include only desired data points.

The sensor can be placed anywhere in the body to measure blood flow. As red blood cells pass each pair of electrodes, the resistance between the pair of electrodes is increased. This creates a spike in the voltage measured across the electrodes. Observing the voltage signal at the first set of electrodes, there will be a spike for each red blood cell. The processing circuitry can count the voltage spikes, giving an indication of hematocrit on a continuous, in vivo basis.

The voltage signal can be measured between every pair of neighboring electrodes. Assuming there is not much change in the cloud of red blood cells, the spike pattern will be similar but delayed by a time, t, at a pair of electrodes further in the direction of blood flow, at a distance, d, from the first electrode pair. By using correlation techniques well known to the ordinary skilled artisan, the voltage signals between each electrode pair can be compared to determine when a specific group of cells passed each point. The velocity can then be computed using the following equation:

$$v = d/t \qquad (1)$$

Using this technique, the blood velocity and hematocrit can be determined at many different points along the sensor. The spacing between electrodes can be provided which is similar to the size of a red blood cell to give the clearest spike for each cell. This allows for the most accurate measure of hematocrit. However, blood velocity can be accurately determined with a much higher spacing using the inventive method. Although the voltage signal would not have as many clear spikes using this alternate approach, the signals at different electrode pairs can still be correlated accurately.

Figure 8:
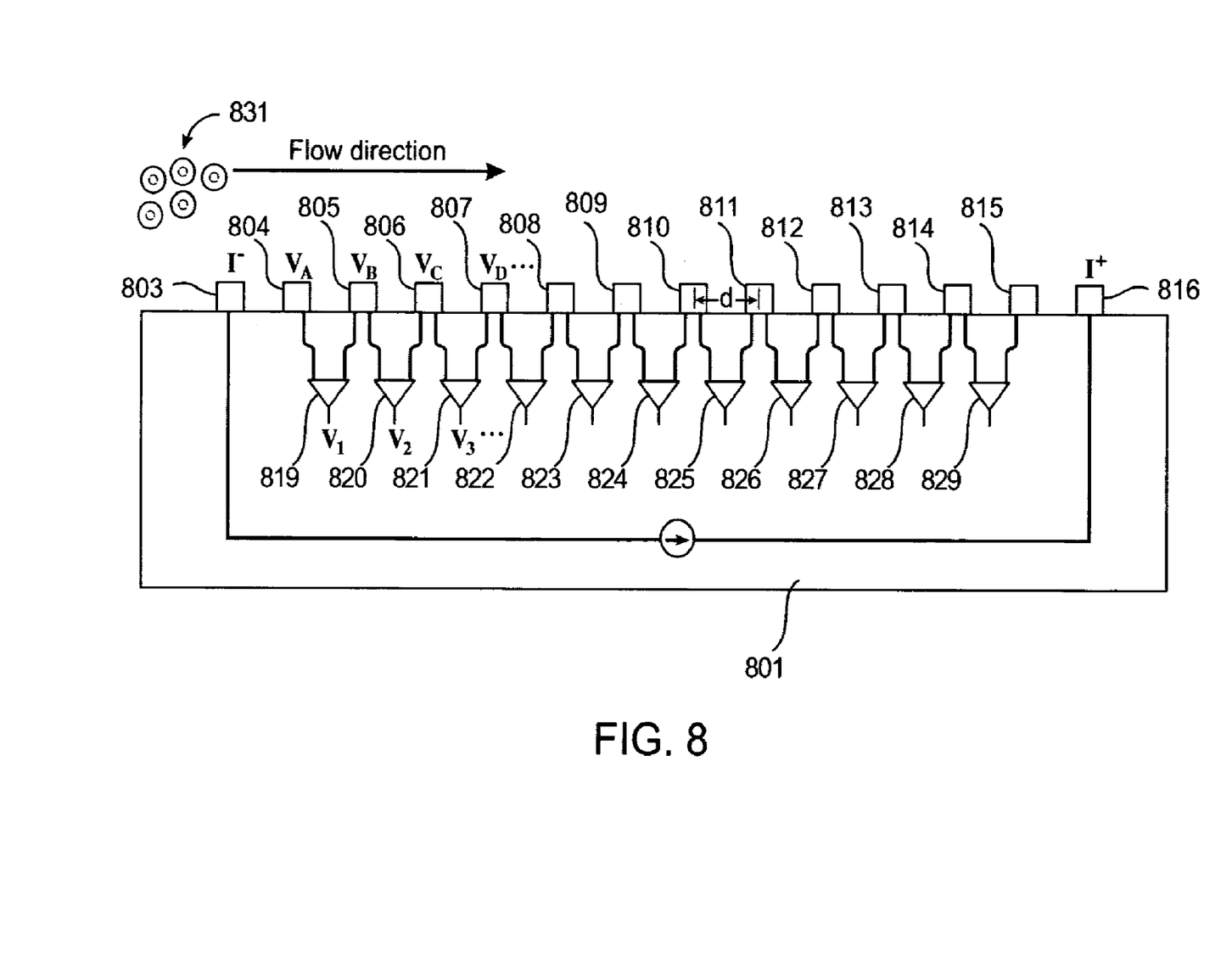
FIG. 8 shows an embodiment of a resistance blood flow sensor according to an embodiment of the present invention.

FIG. 8 shows an embodiment of the inventive blood flow sensor, which consists of a silicon chip 801 with fourteen electrodes 803-816 located on its surface. Each electrode 803-816 is separated by a uniform distance, d. The outermost electrodes 803 and 816 are configured as a current source to drive current through the fluid. The other electrodes 804-815 are configured as voltage sensing electrodes. The voltage signals at all neighboring electrodes are passed through differential amplifiers 819-829 to obtain the voltage difference between the two electrodes. The voltage at the output of each amplifier 819-829 is passed to processing circuitry, where it is analyzed. As red blood cells 831 pass each pair of electrodes, the resistance between the pair of electrodes is increased. This creates a spike in the voltage difference measured between the electrodes.

Figure 9A:
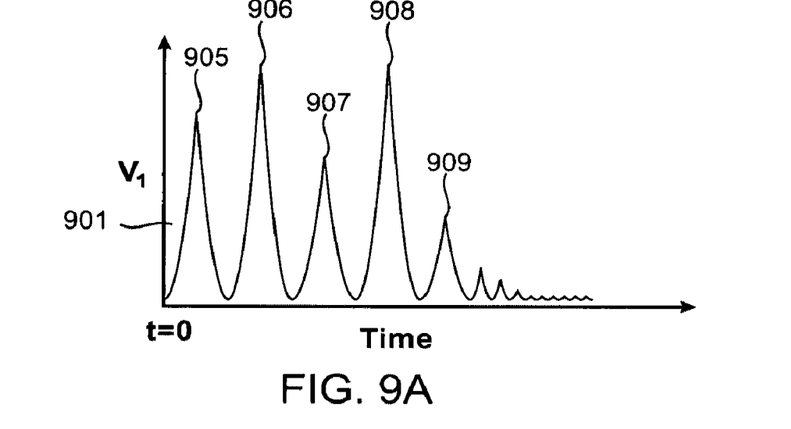
FIGS. 9A to 9C provide depictions of the type of data that may be obtained with a sensor as shown in FIG. 8.

FIG. 9A shows theoretical data for the voltage signal measured by the device shown in FIG. 8 at the output of amplifier 819, which outputs the voltage difference between electrodes 804 and 805. This waveform 901 would be expected when a group of red blood cells passes the pace between electrodes 804 and 805. Each peak 905-909 is caused by one red blood cell passing electrodes 804 and 805. The control circuitry counts the peaks to give an estimation of hematocrit on a continuous, in vivo basis.

Figure 9B:
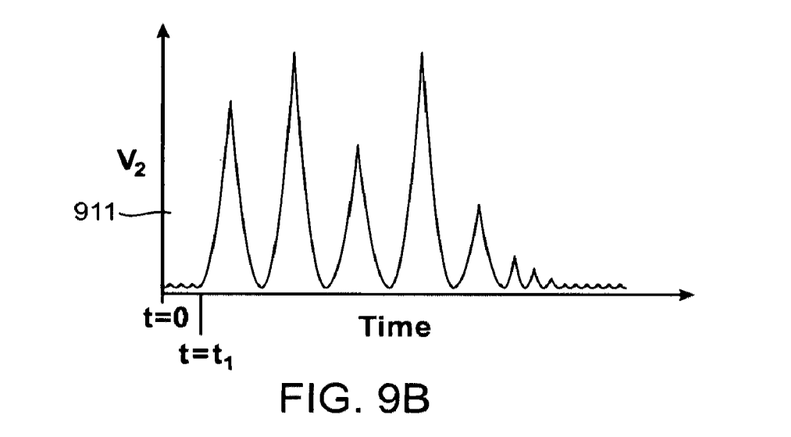

FIG. 9B shows theoretical data for the voltage signal measured by the device shown in FIG. 8 at the output of amplifier 820, which outputs the voltage difference between electrodes 805 and 806. This waveform 911 would be expected when the same group of cells that created waveform 901 from FIG. 9A passes the space between electrodes 805 and 806. Waveform 911 is very similar to waveform 901 in FIG. 9A, except it is delayed by a time, $t_1$. The process circuitry receives waveforms 901 and 911 and correlates them using techniques well known in the art to recognize the analogous waveform, and find the time difference, $t_1$. The velocity, v, of the blood from the area between electrodes 804 and 805 and the area between electrodes 805 and 806 can then be calculated using the following formula:

$$v = d/t_1 \qquad (2)$$

Figure 9C:
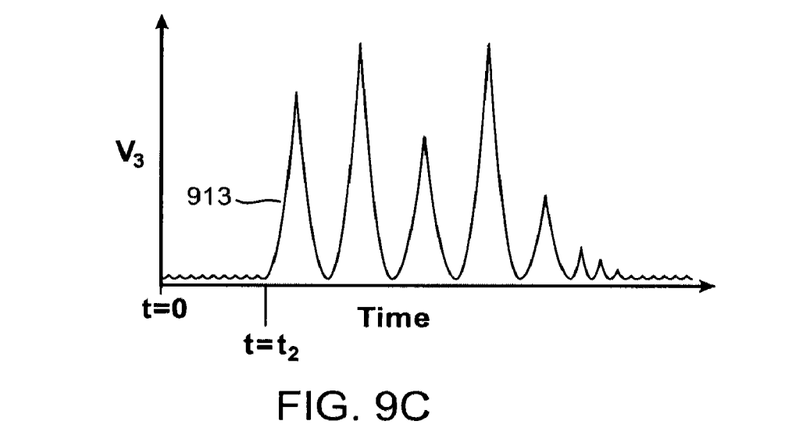

FIG. 9C shows theoretical data for the voltage signal measured by the device shown in FIG. 8 at the output of amplifier 821, which outputs the voltage difference between electrodes 806 and 807. This waveform 913 would be expected when the same group of cells that created waveform 901 from FIG. 9A passes the space between electrodes 806 and 807. The waveform is very similar to waveform 901, except that it is delayed by a time $t_2$. The correlation techniques are used to compare waveform 913 with either waveform 901 from FIG. 9A, waveform 911 from FIG. 9B, or both. This will be used to calculate $t_2$. A roughly instantaneous velocity, v, of the blood from the area between electrodes 805 and 806, and the area between electrodes 806 and 807 can be calculated using the following formula:

$$v = d/(t_2 - t_1) \qquad (3)$$

Alternatively, the average velocity, v, of the blood over a distance of 2 d from the space between electrodes 804 and 805 from the device shown in FIG. 8 and the space between electrodes 806 and 807 can be calculated using the following formula:

$$v = 2d/t_2 \qquad (4)$$

This inventive technique can be used to calculate hematocrit and blood velocity at and between every electrode pair along the length of the sensor. Using different electrode pairs, the spacing between the two data points can be varied depending on the desired information. Each successive neighboring pair can be used to track changes in blood flow over the length of the sensor. Alternatively, for a measure of the average blood flow over the length of the sensor, two electrode pairs that are spaced further apart may be used.

Other features of the cells may also be determined using the inventive sensor. For instance, the shape of the spikes can be used to determine the size of the cells. A larger cell would produce a broader spike, while a smaller cell would produce a sharper spike. By looking at the distribution of the spike width over a large number of cells, statistics such as the relative size of the minor axis of the cell to the major axis of the cell can be generated. This information can be used to evaluate the health of the cells.

It is to be understood that the sensor described herein is illustrative and that variations and modifications are possible. Further, multiple sensors can be implanted at different locations in a patient's circulatory system to measure localized blood flow parameters. All of the sensors may transmit their data directly to a central data collection device (e.g., a pacemaker control can) using wireless signaling as described above. From the central collection point, the data may be processed and/or forwarded to an external device for processing. The data collection device can be internal or external as desired; for instance, a collection device can be implemented as a watch or belt with electrodes that contact the patient's skin while the patient wears the device. An external device may provide audible and/or visual information to the patient or clinician, including alerts, measurement data and the like. Such a device may also include a communication port via which the device can be connected to a computer to which data collected by the device can be transferred.

It should be noted that the sensor embodiment described herein can be implanted and operated for an indefinite period, including while the patient goes about his or her normal activities. Depending on how power is supplied to the sensor, the sensor can be operated continuously or on some duty cycle selected by the clinician. Data reported by the sensors can be stored in the collection device until the patient visits the clinician, at which time the clinician can read out the data and evaluate the patient's condition. In some embodiments, the collection device may also be able to generate an audible or visible alert to the patient if data indicating an abnormal condition are received; the alert prompts the patient to seek medical care.

Applications of Blood Flow Measurements

In another aspect of the invention, a number of physiological parameters can be derived from blood resistivity measurements reported by sensors of the type described herein. These parameters can be used to diagnose a patient's condition, determine a treatment plan, and modify the treatment plan based on the response as determined from continued use of the sensors.

For example, "stroke volume" refers to the amount of blood moved into and out of the heart over a cardiac cycle. In one embodiment, a sensor is positioned to detect flow velocity of blood through a blood vessel located near the heart. From the perspective of accuracy, the aorta is a desirable location for implanting the sensor; however, medical considerations may make an implant into the aorta impractical. The vena cava, which is generally accessible during catheterization procedures, is another suitable site for the implant. The diameter or cross-sectional area of the selected blood vessel at the implant site is measured, e.g., directly (while the vessel is being accessed for the implant), by statistical estimation (e.g., based on an average over a suitable population of patients), by electrical tomography, or by any other suitable technique. The flow rate multiplied by the cross sectional area provides a flux measurement that can be integrated over the duration of a cardiac cycle to determine the total volume of blood passing through the vessel. Stroke volume provides one measure of heart health.

As another example, blood vessel blockages can be detected by implanting a flow sensor in any location where development of a blockage (or worsening of a partial blockage) is anticipated. Occlusion of the blood vessel will affect the blood velocity profile for the vessel, with the effect being stronger as the degree of occlusion increases. Thus, a flow sensor as described herein can be used to monitor a blood vessel for blockages, either acute or chronic. For example, an acute thrombosis could be detected in this manner, with detection triggering an alert to the patient and/or automatic release of an anti-coagulant. Chronic growth of a plaque deposit in a blood vessel can also be measured by detecting changes in the resistivity as the flow rate changes over time.

Additional metrics of heart health can also be defined. For example, as noted above, blood resistivity varies directly with flow velocity and inversely with hematocrit. As a result, it can be difficult to separate the effects of flow velocity and hematocrit on a resistivity measurement. In the short term, hematocrit is effectively constant and this is not an issue, but for longer term monitoring, the possible variation of hematocrit and its effect on resistivity should be considered. Metrics in which the hematocrit dependence is removed (e.g., by cancellation in a ratio) can advantageously be used to facilitate long-term monitoring of changes in heart health. For instance, if $v_{max}$ is the maximum flow velocity during a cardiac cycle and $v_{min}$ is the minimum flow velocity, one can define a flow ratio $\eta$ as:

$$\eta = \frac{v_{max}}{v_{min}}. \tag{5}$$

One might expect $\eta$ to be large for a healthy heart and small for a weak or diseased heart. An advantage of such a metric is that in resistivity-based blood flow sensors (e.g., as described above), it can be difficult to disentangle the effects of flow velocity and hematocrit; in Eq. (5), any hematocrit dependencies would cancel out. Other similar metrics could also be constructed and validated through clinical observation.

In other embodiments, hematocrit and flow are measured separately. In one embodiment, hematocrit is determined by measuring resistivity in a region where flow velocity is known (and preferably fixed). In another embodiment, small flow sensors detect the passage of individual red blood cells. For instance, the sensor embodiment shown in FIG. 1 above can be fabricated on a semiconductor substrate with the distance S in the 6-8 micron range.

For a semi-infinite medium, the voltage V measured by a device of this kind is given by:

$$V = \frac{\rho I}{2\pi S}, \tag{6}$$

where $\rho$ is the resistivity of the medium and I is the applied current. (See Barber & Brown, *J. Phys. E. Sci. Instrum.*, 17, 723 (1984).) In physiological situations, the approximation of a semi-infinite medium can be questionable, but Eq. (6) becomes reliable as the device size S becomes small relative to other dimensions (e.g., diameter of the blood vessel). In this context, departures from Eq. (6) will tend to be characterized by a geometrical factor of order unity, making the approximation reliable.

When the dimension S becomes comparable to the size of a red blood cell (RBC), a new effect becomes detectable. As individual RBCs pass close to the sensor, they create discrete disruptions in the potential field, analogous to shot noise in electronic circuits. This effect may be used to count individual RBCs, giving an absolute measure of hematocrit. The variation in the resistance arising from different orientations of the RBCs gives a measurement of the flow, separating the hematocrit and flow-velocity effects on resistivity. These two parameters can then be used as distinct measures of a patient's health.

In other embodiments, blood flow sensors are used in detection of injury (e.g., bleeding) and wound management. Any injury that results in internal or external bleeding will also change the flow profile in blood vessels surrounding the injury site. According, flow sensors can be implanted at or near an injury site or surgical site to detect whether bleeding has stopped. In the case of surgical sites, it may be useful to implant such sensors to detect internal bleeding after the surgery so that action can be taken even before symptoms are apparent.

Still other embodiments use blood flow as an indicator of physiological activity in body tissues or organs to which blood is supplied. It is generally known that as systems, organs or tissues in the body become more active, blood flow to those locations increases in order to satisfy the increased metabolic demand. For instance, blood flow to various areas of the brain increases when those areas are active (e.g., during various kinds of mental activity). Blood flow sensors in or around the brain could be used to detect such activity and to associate various mental activities with the relevant regions of the brain. Absence of increased blood flow in situations where it would be expected may also indicate an abnormality.

In a related embodiment, sensors as described herein might be used to construct a "lie detector." By studying subjects engaged in deceptive and non-deceptive behavior, it may be possible to identify characteristic differences in blood flow patterns (e.g., certain areas of the brain might become more active); these differences could be used to detect deceptive behavior in other subjects.

Similarly, the stomach and intestines receive increased blood flow during digestion; thus, digestive processes can be detected and monitored using sensors placed in gastric blood vessels.

Abnormal tissues, such as malignant tumors, can also be monitored, as blood flow to the tumor will depend on the size of the tumor and whether it is growing or shrinking. Changes in blood flow in a vessel feeding the tumor can provide an indication as to how effectively a given course of treatment is working. This information can be used by a clinician in determining whether to continue or change the treatment.

It will be appreciated that the uses described herein are illustrative and that the invention is not restricted to particular uses for blood flow measurements.

EXAMPLE

Blood Flow in Vena Cava

An experiment was performed using a blood flow sensor of the type described herein. The experimental setup and results are presented by way of illustrating the efficacy of an embodiment of the present invention, and this description is not intended to limit the scope of the claims.

Figure 4:
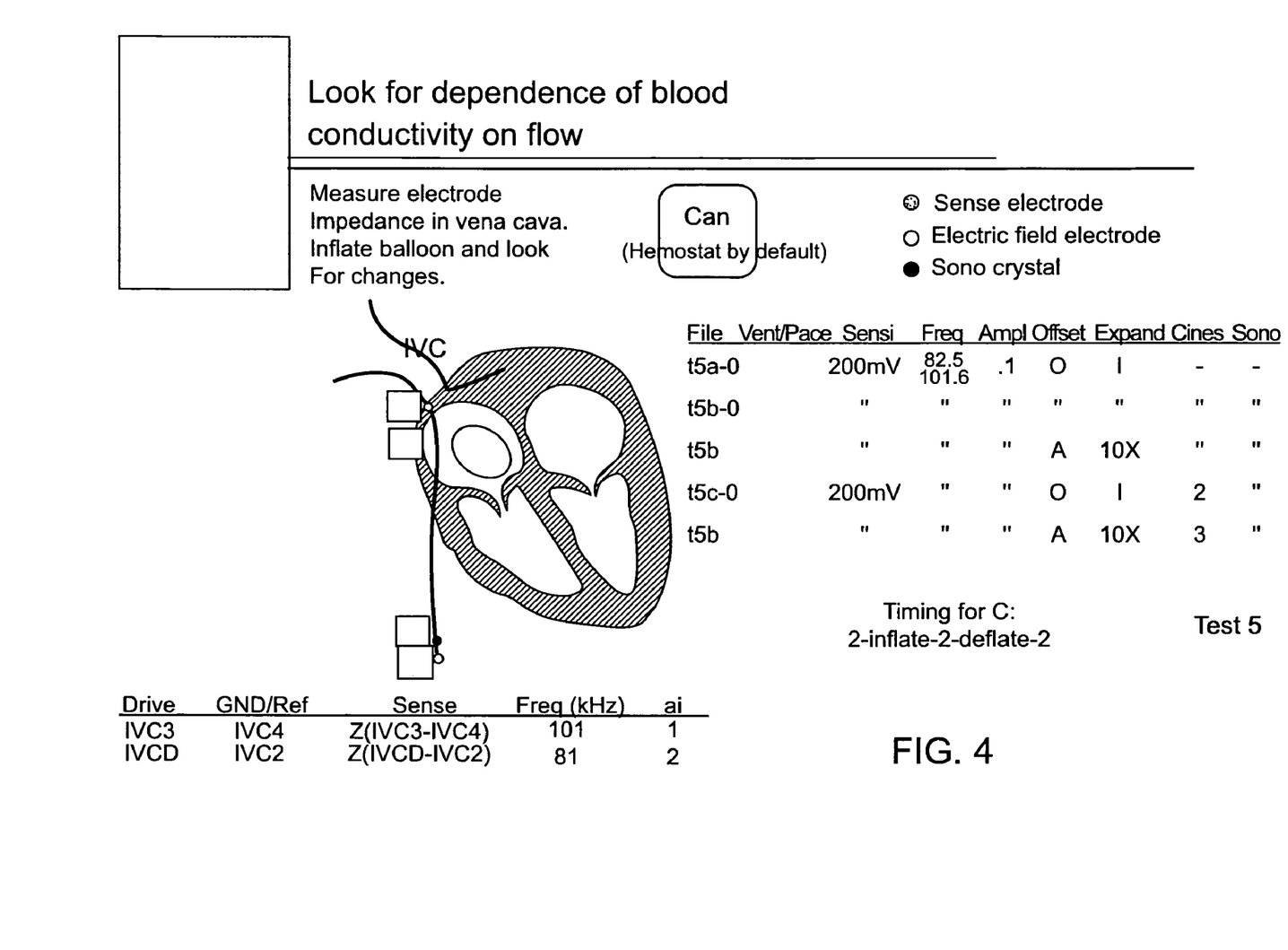
FIG. 4 illustrates an experimental setup for testing a blood resistivity sensor according to an embodiment of the present invention.

FIG. 4 illustrates an experimental setup for testing a blood resistivity sensor according to an embodiment of the present invention. Using a pig as the test subject, one sensor (with a pair of electrodes) was placed in the superior vena cava (SVC) and another in the inferior vena cava (IVC), and a two-point measurement was performed. Constant voltage was applied between each pair of electrodes, and the voltage across a 10-ohm resistor in series was measured. The measured voltage is proportional to current and thus inversely proportional to impedance between the two electrodes in the pair.

Figure 5:
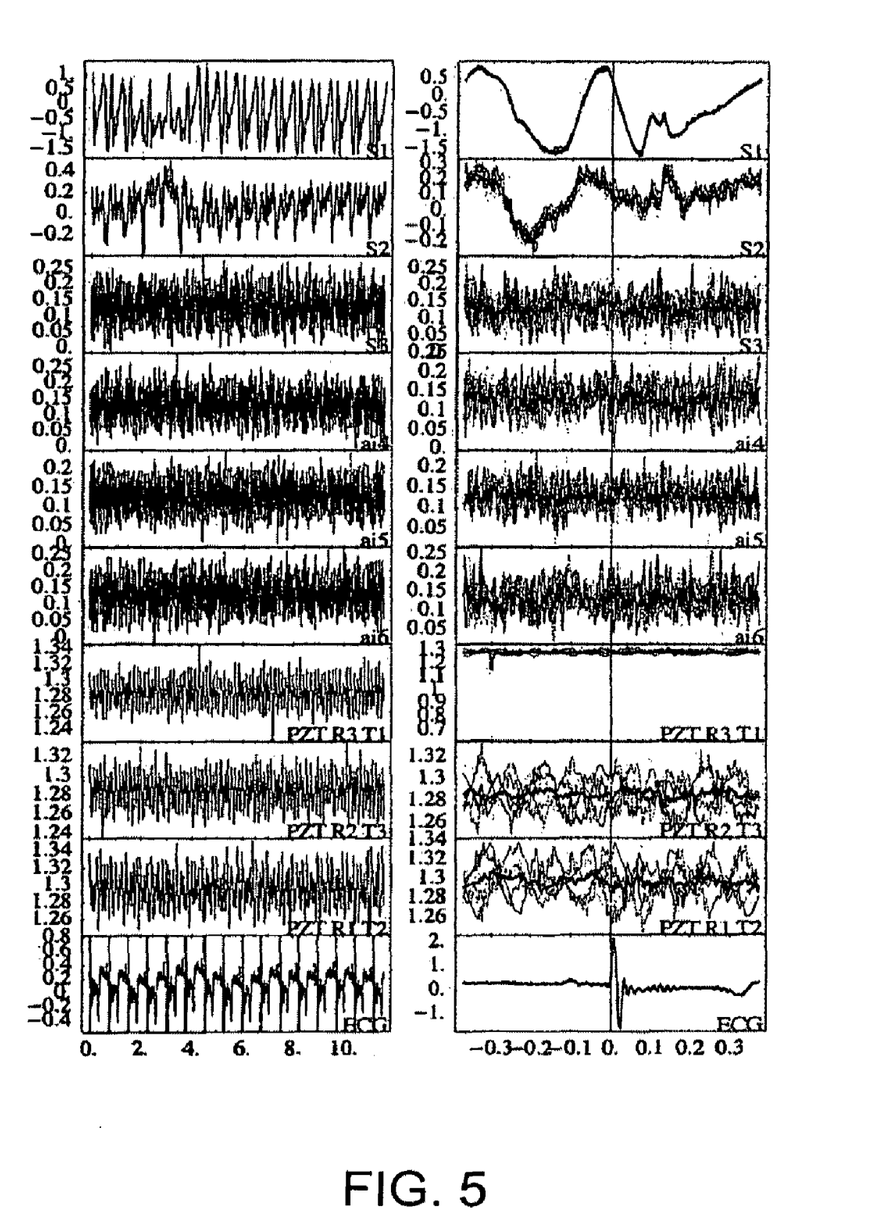
FIGS. 5-7 are results obtained from experiments conducted using the setup of FIG. 4.
Figure 6:
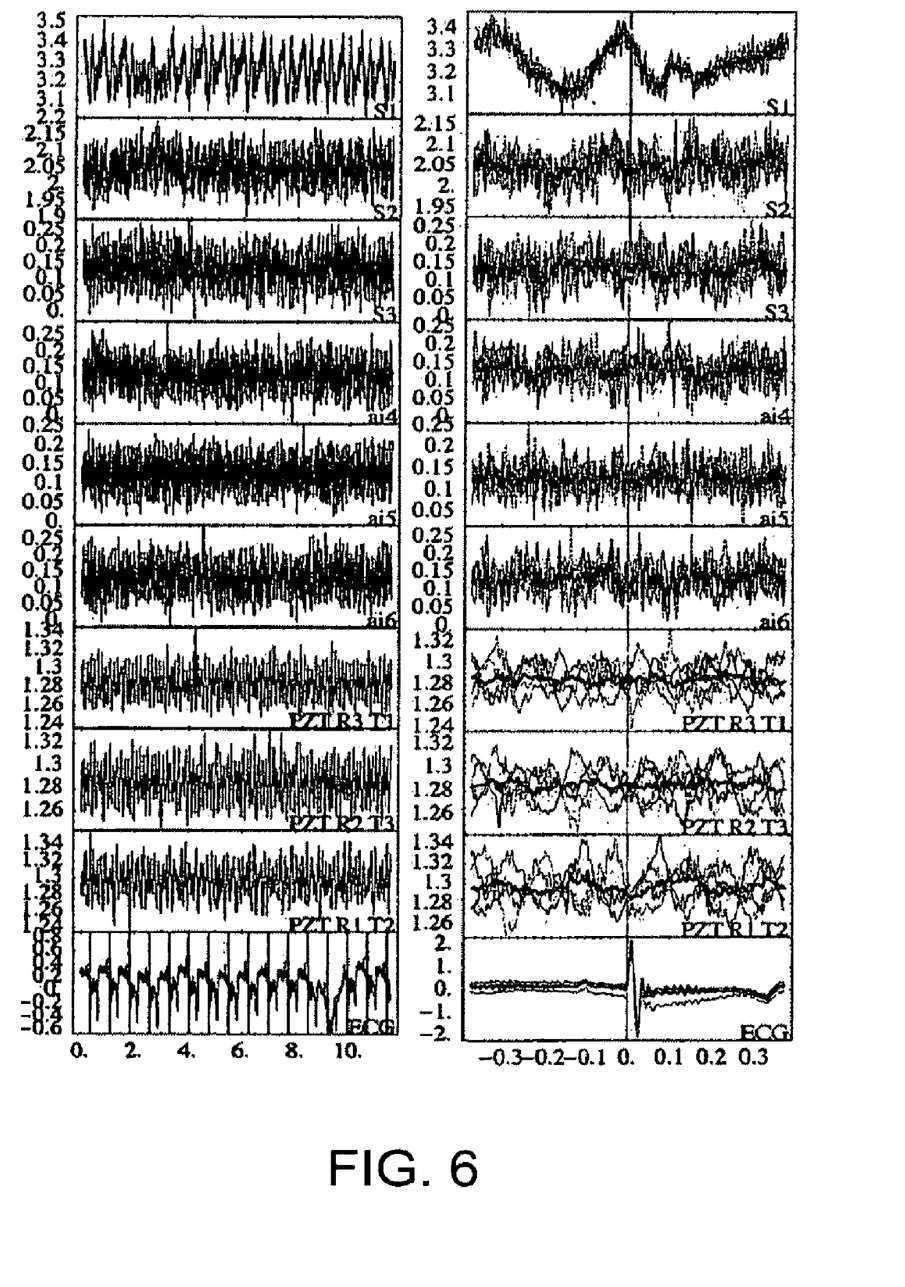

FIGS. 5 and 6 are results obtained from experiments in an anesthetized pig. The top panel (S1) corresponds to the SVC, and the second panel (S2) corresponds to the IVC. The bottom panel (ECG) corresponds to an electrocardiogram taken at the same time as the data. Panels in the left column show a time trace of about 12 seconds, and the right column shows data for several cardiac cycles (as determined from the ECG readings) overlaid.

In this setup, it is expected that increased blood velocity should correspond to more positive readings, and indeed one sees that the blood velocity varies systematically across a cardiac cycle.

Figure 7:
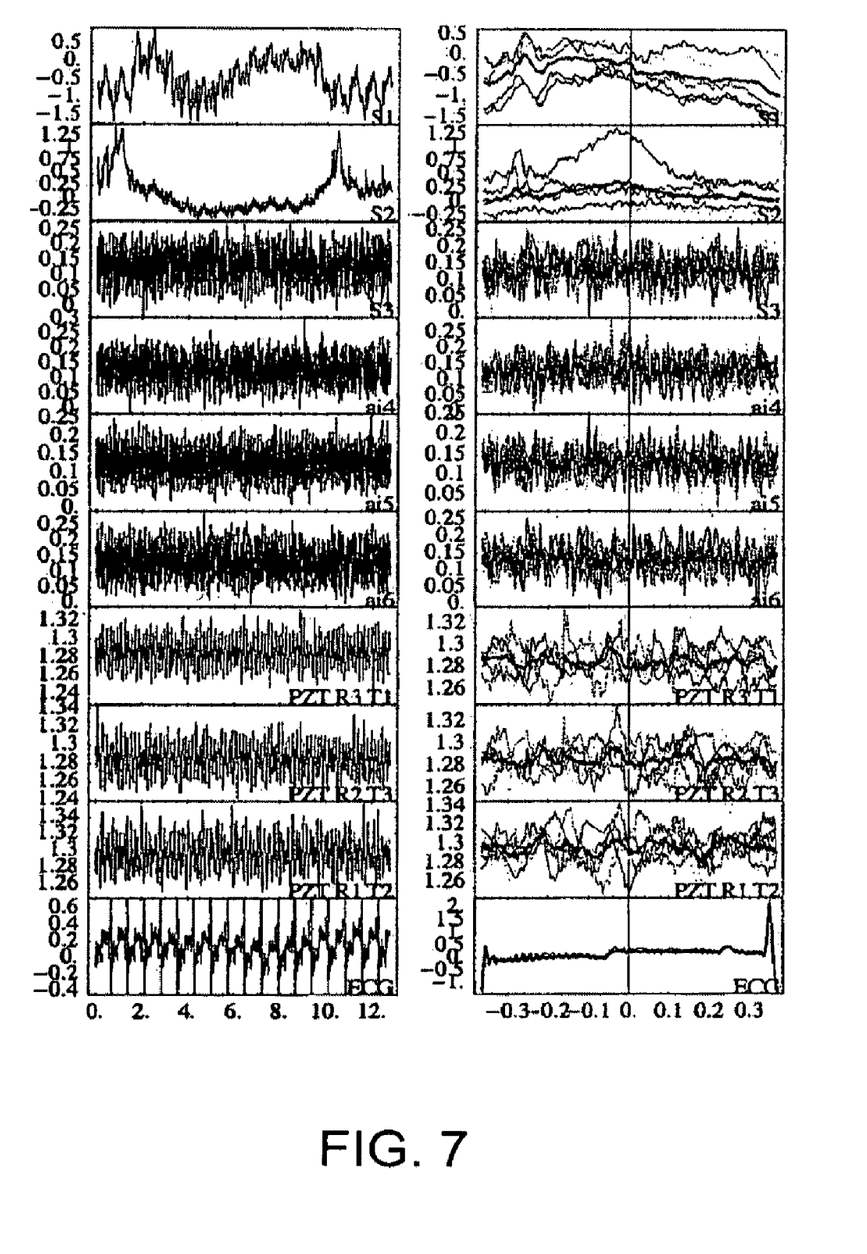

FIG. 7 shows results from an experiment in which a balloon was inflated to occlude the IVC, blocking blood flow. The experiment began with the balloon deflated; after about 2 seconds, the balloon was inflated over 2-3 seconds, held full for 2 seconds, then deflated over 2-3 seconds.

The SVC panel (S1) shows that the flow rate in the SVC generally increased when the IVC was blocked, since the SVC must provide more blood to fill the heart when the IVC is blocked. When the IVC was unblocked, restoring the flow, the flow rate in the SVC decreased. The dip at around 4 seconds is believed to be due to a systemic effect: the increased flow "sucked the SVC dry" until hemodynamic systems could compensate.

The IVC panel (S2) shows that the flow rate in the IVC spiked as the vessel was pinched off by the inflating balloon, with blood rushing through the narrow opening between the vessel wall and the balloon. The blood flow generally decreased below baseline (see FIGS. 5 and 6) when the vessel was completely blocked, although the effect is not as dramatic as might have been expected. The results also show that the variation of flow rate within a cardiac cycle is decreased when the vessel is occluded.

Thus, measuring electrical resistivity (or conductivity) as described herein is a viable tool for monitoring the patient's circulatory system, including the development of vessel blockages.

Although the invention has been described with respect to specific embodiments, it will be appreciated that the invention is intended to cover all modifications and equivalents within the scope of the following claims.

What is claimed is:

1. An implantable blood flow sensor to generate signals used to simultaneously determine a velocity and hematocrit of flowing blood, the implantable blood flow sensor comprising:
    a substrate sized and shaped to be implantable in a blood vessel of a body of a patient;
    a pair of current-flow terminals disposed on a top surface of the substrate and arranged to be placed in the flowing blood;
    a current source fabricated on the substrate and configured to transfer charge between the pair of current-flow terminals;
    at least three sense electrodes disposed on the top surface of the substrate substantially in line with each other between the current-flow terminals with each sense electrode of the at least three sense electrodes separated from a neighboring sense electrode by a distance S, wherein the at least three sense electrodes comprise a first pair of neighboring sense electrodes formed by a first sense electrode and a second sense electrode adjacent to the first sense electrode and a second pair of neighboring sense electrodes formed by the second sense electrode and a third sense electrode adjacent to the second sense electrode; and
    a detection circuit fabricated on the substrate, electrically coupled to the at least three sense electrodes, and configured to generate at least a first signal based on a potential difference between the first pair of neighboring sense electrodes and a second signal based on a potential difference between the second pair of neighboring sense electrodes, wherein the velocity of the flowing blood is determined based on a distance between the first pair of neighboring sense electrodes and the second pair of neighboring sense electrodes in addition to a time shift between the first signal and the second signal, and wherein the hematocrit of the flowing blood is determined by counting a number of spikes in the first signal or the second signal, the number of spikes corresponding to red blood cells passing via the first pair of the neighboring sense electrodes or the second pair of the neighboring sense electrodes.

2. The implantable blood flow sensor of claim 1 further comprising:
    a transmitter unit coupled to an output node of the detection circuit and configured to transmit the at least first signal and the second signal to a data collector.

3. The implantable blow flow sensor of claim 2 wherein the transmitter unit is configured to transmit via quasi-electrostatic coupling into a conductive tissue of the body of the patient.

4. The implantable blood flow sensor of claim 2 wherein the transmitter is fabricated on the substrate.

5. The implantable blood flow sensor of claim 1 further comprising a power supply unit coupled to the current source, wherein the power supply unit is configured to supply power to the current source and the detection circuit.

6. The implantable blood flow sensor of claim 5 wherein the power supply unit is further configured to receive power via a quasi-electrostatic coupling to a conductive tissue of the body.

7. The implantable blood flow sensor of claim 1 wherein the distance S is set as similar to a size of a red blood cell.

8. The implantable blood flow sensor of claim 7 wherein the distance S is between about 6 and about 8 microns.

9. The implantable blood flow sensor of claim 1, wherein the detection circuit comprises at least two differential amplifiers.

10. A method of measuring a physiological parameter, the method comprising:
   implanting a blood flow sensor in a blood vessel in a body of a patient, the blood flow sensor configured to measure and transmit a velocity and hematocrit of flowing blood in the blood vessel, wherein the blood flow sensor comprises:
   a substrate sized and shaped to be implantable in the blood vessel;
   a pair of current-flow terminals disposed on a to surface of the substrate and arranged to be placed in the flowing blood;
   a current source fabricated on the substrate and configured to transfer charge between the pair of current-flow terminals;
   at least three sense electrodes disposed on the top surface of the substrate substantially in line with each other between the current-flow terminals with each sense electrode of the at least three sense electrodes separated from a neighboring sense electrode by a distance S, wherein the at least three sense electrodes comprise a first pair of neighboring sense electrodes formed by a first sense electrode and a second sense electrode adjacent to the first sense electrode and a second pair of neighboring sense electrodes formed by the second sense electrode and a third sense electrode adjacent to the second sense electrode; and
   a detection circuit fabricated on the substrate, electrically coupled to the at least three sense electrodes, and configured to generate at least a first signal based on a potential difference between the first pair of neighboring sense electrodes and a second signal based on a potential difference between the second pair of neighboring sense electrodes, wherein the velocity of the flowing blood is determined based on a distance between the first pair of neighboring sense electrodes and the second pair of neighboring sense electrodes in addition to a time shift between the first signal and the second signal, and wherein the hematocrit of the flowing blood is determined by counting a number of spikes in the first signal or the second signal, the number of spikes corresponding to red blood cells passing via the first pair of neighboring sense electrodes or the second pair of neighboring sense electrodes;
   communicably coupling a data collector to the blood flow sensor, wherein the data collector is implanted in or attached to the body of the patient;
   operating the blood flow sensor to measure the velocity and the hematocrit and transmit the velocity and the hematocrit to the data collector; and
   processing the velocity and the hematocrit to extract the physiological parameter.

11. The method of claim 10 wherein the blood flow sensor is configured to communicate wirelessly using quasi-electrostatic coupling to a conductive tissue of the body of the patient.

12. The method of claim 11 wherein the data collector comprises a pacemaker can configured to detect quasi-electrostatic signals propagating in the body of the patient.

13. The method of claim 11 wherein the data collector comprises a wearable unit including electrodes attachable to the skin of the patient and configured to detect quasi-electrostatic signals propagating in the body of the patient.

14. The method of claim 10 wherein the blood flow sensor is operated while the patient is away from a medical clinic.

15. The method of claim 10 further comprising:
   triggering a remedial action based on the physiological parameter.

16. The method of claim 15 wherein the remedial action includes releasing a medication into the body of the patient.

17. The method of claim 15 wherein the remedial action includes alerting the patient to seek medical attention.

* * * * *